United States Patent
Buckley et al.

(10) Patent No.: US 11,231,339 B2
(45) Date of Patent: Jan. 25, 2022

(54) SYSTEMS AND METHODS FOR DETERMINING A THICKNESS OF A NONAQUEOUS PHASE LIQUID LAYER

(71) Applicant: AECOM, Los Angeles, CA (US)

(72) Inventors: Daniel Avery Buckley, Long Beach, CA (US); Brad William Koons, North Oaks, MN (US); Steven Thomas Gaito, South Easton, MA (US); Monal Gajjar, Cerritos, CA (US)

(73) Assignee: AECOM, Los Angeles, CA (US)

( * ) Notice: Subject to any disclaimer, the term of this patent is extended or adjusted under 35 U.S.C. 154(b) by 99 days.

(21) Appl. No.: 16/353,524

(22) Filed: Mar. 14, 2019

(65) Prior Publication Data

US 2019/0285497 A1 Sep. 19, 2019

Related U.S. Application Data

(60) Provisional application No. 62/644,334, filed on Mar. 16, 2018.

(51) Int. Cl.
*G01L 19/08* (2006.01)
*G01N 33/28* (2006.01)

(52) U.S. Cl.
CPC .............. *G01L 19/08* (2013.01); *G01N 33/28* (2013.01)

(58) Field of Classification Search
CPC ...... G01F 23/0038; G01F 23/14; G01F 23/18; G01F 23/2963; G01F 23/72; G01F 23/74; G01F 23/76; G01F 23/00; G01N 11/00; G01N 33/28; G01N 33/2835; G01N 2291/02854; G01N 33/1833; G01N 33/2847; G01N 33/26; G01N 2291/0226; G01N 2015/0668; G01N 33/03;
(Continued)

(56) References Cited

U.S. PATENT DOCUMENTS 3,935,741 A * 2/1976 Zinsmeyer .............. G01F 23/68
 73/313
4,976,146 A * 12/1990 Senghaas ................ G01F 23/74
 200/84 C (Continued)

FOREIGN PATENT DOCUMENTS

WO WO 2016/141202 A1 9/2016

OTHER PUBLICATIONS

ASTM E2856-13, Standard Guide for Estimation of LNAPL Transmissivity, ASTM International, West Conshohocken, PA, 2013, www.astm.org, 68 pages.

(Continued)

*Primary Examiner* — John Fitzgerald
*Assistant Examiner* — Truong D Phan
(74) *Attorney, Agent, or Firm* — Knobbe, Martens, Olson & Bear, LLP (57) ABSTRACT

Various embodiments relate to systems and methods for determining a thickness of a nonaqueous phase liquid layer (NAPL) that is disposed adjacent a second layer of aqueous phase liquid (APL). The system can include a pressure transducer assembly having a total density value between a first density value of the NAPL and a second density value of the APL. The pressure transducer assembly can be configured to measure a first pressure associated with the pressure exerted by the first layer.

27 Claims, 5 Drawing Sheets

(58) Field of Classification Search
CPC .. G01N 33/22; G01N 33/241; G01N 33/2823; G01L 19/08
See application file for complete search history.

(56) References Cited

U.S. PATENT DOCUMENTS

| | | | | |
|---|---|---|---|---|
| 5,950,487 A * | 9/1999 | Maresca, Jr. | ......... | G01F 23/686 73/293 |
| 6,928,862 B1 * | 8/2005 | Robbins | ................. | G01F 23/14 73/299 |
| 7,730,779 B2 * | 6/2010 | Mahadevaiah | ..... | G01F 23/0038 73/291 |
| 8,286,483 B2 * | 10/2012 | Mahadevaiah | ......... | G01F 23/18 73/290 R |
| 8,656,774 B2 * | 2/2014 | Moss | ...................... | G01F 23/00 73/440 |
| 2007/0251316 A1 * | 11/2007 | Mahadevaiah | ......... | G01F 23/72 73/299 |
| 2009/0126483 A1 | 5/2009 | Blendinger et al. | | |
| 2009/0277844 A1 | 11/2009 | Panter | | |
| 2010/0218601 A1 * | 9/2010 | Mahadevaiah | ......... | G01F 23/74 73/299 |
| 2011/0112773 A1 * | 5/2011 | Atkinson | ................ | G01F 1/663 702/47 |

OTHER PUBLICATIONS

GeoStream UK, "Introducing NAPLsense by GeoStream—a continuous monitoring system for measuring oil on groundwater," https://www.remediation.com/geostream-latest-news/news-items/geostream-uk-launches-new-monitoring-system-for-measuring-contaminated-oil.html, downloaded Jun. 3, 2019, 5 pages.
International Search Report and Written Opinion dated Jul. 12, 2019, for International Application No. PCT/US2019/022301, in 16 pages.

* cited by examiner

SYSTEMS AND METHODS FOR DETERMINING A THICKNESS OF A NONAQUEOUS PHASE LIQUID LAYER

CROSS-REFERENCE TO RELATED APPLICATIONS

This application claims priority to U.S. Provisional Patent Application No. 62/644,334, filed Mar. 16, 2018, the entire contents of which are hereby incorporated by reference herein in their entirety and for all purposes.

BACKGROUND

Field of the Invention

The field relates to systems and methods for determining a thickness of a nonaqueous phase liquid (NAPL) layer.

Description of the Related Art

Nonaqueous phase liquids (NAPLs), such as light, nonaqueous phase liquids (LNAPLs) or dense, nonaqueous phase liquids (DNAPLs), are common environmental contaminants that are immiscible with, minimally soluble in, and having a density that is different from that of water. LNAPLs are a type of NAPL having a density less than that of water. By contrast, dense nonaqueous phase liquids (DNAPLs) have a density greater than that of water.

Examples of LNAPLs include hydrocarbons, such as benzene, diesel, gasoline, toluene, and xylene. When a sufficient volume of LNAPLs is released into the environment, the LNAPLs will migrate vertically until they reach the water table, where buoyancy forces and increasing water content halt their movement. LNAPLs exist in a complex multiphase domain within the subsurface where LNAPL and groundwater are intermingled. When groundwater monitoring wells are placed in LNAPL-affected soil at environmental sites, the LNAPLs and groundwater that enter the wells separate and form a distinct, floating layer above water within the monitoring wells. Because common LNAPLs are oftentimes oils, the upper surface (e.g., an air/LNAPL surface or interface) and lower surface (e.g., LNAPL/water surface or interface) of a floating LNAPL layer in a monitoring well are frequently called the "air/oil" (or air/LNAPL) and "oil/water" (or LNAPL/water) interfaces, respectively. Collectively, the air/LNAPL and LNAPL/water surfaces are frequently referred to as the fluid level interfaces.

Remediation regulations often require the removal of LNAPL contaminants from the environment. These regulations frequently mandate LNAPL removal based on the thickness of LNAPL layers in monitoring wells, as opposed to the concentration of LNAPL components in an environmental medium (e.g., groundwater); in any case due to immiscibility the actual concentration is often fairly low. Moreover, the thickness of LNAPL layers in monitoring wells is often used to measure the success of any environmental remediation efforts. Thus, to properly assess remedial progress, instruments and methods are used to ascertain thicknesses of LNAPL layers.

The thicknesses of LNAPL layers are typically measured by manually determining the physical locations of the fluid level interfaces in a well employing equipment such as oil/water interface probes (manual gauging). During manual gauging, an oil/water interface probe senses changes in dielectric and/or optical properties within the surrounding fluid, and indicates, through either sound and/or light, whether the probe is immersed in air, LNAPL, or water.

Manual gauging, as its name implies, uses human labor. This may give rise to various problems. For example, manual gauging may require a significant amount of field labor and may incur high labor costs. Moreover, monitoring wells located in high hazard areas (e.g., those near active rail lines, those adjacent to refinery process units, etc.) may expose field staff to health and safety risks. Also, limited field staff availability and/or site access may create situations where insufficient data are collected during the allowable work period to produce an acceptable data set. Furthermore, manual measurements may not be collected quickly enough to adequately characterize rapid hydraulic responses. In addition, manual gauging can also suffer from potential data quality issues, which may stem from, inter alia, low precision of manual measurements and/or human error.

The efficacy of the oil/water interface probes used in manual gauging may also be complicated by the fact that an LNAPL may have dielectric and/or optical properties that are not compliant with the probe's set points, as established by its manufacturer. Also, high-viscosity LNAPLs may coat the oil/water interface probe and preclude the probe from differentiating between LNAPL and water.

Instruments and methods for automatically and/or remotely measuring LNAPL thicknesses are also known in the art. Automated tools to sense the air/LNAPL and/or LNAPL/water interfaces in a monitoring well have been developed. For example, one method teaches the usage of a sensor that measures (1) the total head pressure exerted by both LNAPL and water and (2) the physical location of the air/LNAPL interface. From these two values, an LNAPL layer thickness can be calculated. In one embodiment of this method, the total head pressure is measured through a pressure sensor, mounted at a fixed depth, and the physical location of the air/LNAPL interface is determined through a pressure-sensitive tape, also mounted at a fixed depth, with a printed-circuit configuration, such that the tape acts as a variable electrical resistor when immersed in fluid. This method may also have difficulties. For example, the equipment for practicing this method may be relatively costly to fabricate, and components, such as the tape, may have durability and reliability issues that may be exacerbated by rough handling. Also, above grade equipment for this method may require protection. Moreover, users of this method may encounter difficulties deploying the necessary equipment. Additionally, when either the water and/or the LNAPL level varies significantly (e.g., when there is rain that causes ground water table rise), the user may have to manually relocate the tape and/or the pressure sensor. Data quality may suffer if the LNAPL is viscous, so as to coat the tape and interfere with the determination of the physical location of the air/LNAPL interface.

LNAPL thickness data can also be collected remotely by deploying within monitoring wells multiple submersible pressure transducers (pressure sensors) at fixed depths that measure and log pressure data automatically at programmed intervals. For a well in which both water and LNAPL are present, data collected by a transducer deployed within the water column represents total head pressure exerted by both fluids, whereas data collected by a transducer deployed within the LNAPL column represents LNAPL head pressure only. The difference between the total head pressure and the LNAPL head pressure can be used to calculate the thickness of an LNAPL layer. However, like manual gauging, this method may also present data quality challenges because pressure transducers do not differentiate between pressures exerted by different fluids (i.e., LNAPL and water). Thus, if the water level rises (e.g., during dynamic tests) this method may produce either inadequate or inaccurate data. Illustratively, if the transducer measuring LNAPL head pressure (the LNAPL transducer) is deployed too deeply, it could become submerged in water, at which point its pressure data would represent both LNAPL and water head pressure and no longer be useful for determining LNAPL thickness. Moreover, if the LNAPL layer thickness is too small, the LNAPL transducer may be deployed too shallow, such that the transducer may not capture the actual LNAPL head pressure.

Accordingly, there remains a continuing need for improved systems and methods for determining a thickness of a nonaqueous phase liquid layer.

SUMMARY

In one embodiment, a method for measuring a thickness of a first layer of nonaqueous phase liquid (NAPL) that is disposed adjacent a second layer of aqueous phase liquid (APL) is disclosed. An interface between the first and second layers can be located at a first depth relative to a reference position. The method can include determining a first pressure exerted by the first layer with a first pressure transducer assembly including a first pressure transducer. The first pressure transducer assembly can have a total density value between a first density value of the NAPL and a second density value of the APL. The method can include calculating the thickness of the first layer based at least in part on the determined first pressure.

In another embodiment, a method for measuring a thickness of a first layer of nonaqueous phase liquid (NAPL) that is disposed adjacent a second layer of aqueous phase liquid (APL) is disclosed. An interface between the first and second layers can be located at a first depth relative to a reference position. The method can include determining a first pressure exerted by the first layer with a first pressure transducer assembly including a first pressure transducer, wherein the first pressure transducer assembly floats with the interface. The method can include calculating the thickness of the first layer based at least in part on the determined first pressure.

In another embodiment, a system for measuring a thickness of a first layer of nonaqueous phase liquid (NAPL) that is disposed adjacent a second layer of aqueous phase liquid (APL) is disclosed. An interface between the first and second layers can be located at a first depth relative to a reference position. The system can include a pressure transducer assembly having a total density value between a first density value of a target NAPL and a second density value of a target APL. The pressure transducer assembly can be configured to measure a first pressure associated with the pressure exerted by the first layer.

In another embodiment, a system for measuring a thickness of a first layer of nonaqueous phase liquid (NAPL) that is disposed adjacent a second layer of aqueous phase liquid (APL) is disclosed. An interface between the first and second layers can be located at a first depth relative to a reference position. The system can include a pressure transducer assembly having a total density value in a range of 0.6 g/cc to 0.999 g/cc. The pressure transducer assembly can include a first pressure transducer configured to measure a first pressure associated with the pressure exerted by the first layer.

In another embodiment, a system for measuring a thickness of a first layer of nonaqueous phase liquid (NAPL) that is disposed adjacent a second layer of aqueous phase liquid (APL) is disclosed. An interface between the first and second layers can be located at a first depth relative to a reference position. The system can include a pressure transducer assembly having a total density value in a range of 1.001 g/cc to 6 g/cc. The pressure transducer assembly can include a first pressure transducer configured to measure a first pressure associated with the pressure exerted by the first layer.

In another embodiment, a system for measuring a thickness of a first layer of nonaqueous phase liquid (NAPL) that is disposed adjacent a second layer of aqueous phase liquid (APL) is disclosed. An interface between the first and second layers can be located at a first depth relative to a reference position. The system can include a pressure transducer assembly having an adjustable total density value, the adjustable total density value configured to be adjusted to a value between a first density value of a target NAPL and a second density value of a target APL. The pressure transducer assembly can include a first pressure transducer configured to measure a first pressure associated with the pressure exerted by the first layer.

In another embodiment, a method of assembling a pressure transducer assembly for measuring a thickness of a first layer of nonaqueous phase liquid (NAPL) that is disposed adjacent a second layer of aqueous phase liquid (APL) is disclosed. The method can include determining a first density of the NAPL. The method can include determining a second density of the APL. The method can include adjusting a total density of the pressure transducer assembly to have a value between the first density and the second density.

In another embodiment, a system for measuring a thickness of a layer of nonaqueous phase liquid is disclosed. The system can include a first pressure transducer attached to a floatable member, such that a total density of the first pressure transducer and the floatable member exceeds a density of a first layer of nonaqueous liquid but is less than a density of a second layer of aqueous liquid, such that the first pressure transducer is capable of measuring a pressure exerted by the layer of nonaqueous liquid. The system can include a second pressure transducer for measuring a total pressure exerted by the layer of nonaqueous liquid and by the layer of aqueous liquid, wherein both the first and the second pressure transducers have activated data logging capabilities.

In another embodiment, a method for measuring a thickness of a layer of nonaqueous phase liquid is disclosed. The method can include determining a pressure exerted by the layer of nonaqueous phase liquid with a first pressure transducer. A distance between the first pressure transducer and an interface between the layer of nonaqueous phase liquid and the layer of aqueous phase liquid can remain constant after movement of the interface such that the first pressure transducer floats with the interface. The method can include determining a total pressure exerted by the layer of nonaqueous liquid and by the layer of aqueous phase liquid with a second pressure transducer. The method can include calculating a difference in depths between the layer of nonaqueous phase liquid and the layer of aqueous phase liquid.

DETAILED DESCRIPTION

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a system and method of fluid level measurement using a pressure transducer deployed at a fixed depth and a second pressure transducer whose depth is variable but with a fixed relation to the NAPL/water interface.

The systems and methods of the present embodiments represent a different approach that is superior to other techniques because it can enable the remote and/or automatic calculation of NAPL layer thickness (such as a LNAPL layer thickness, or a DNAPL layer thickness), so as to ameliorate the issues presented by manual gauging. Moreover, unlike other methods of remotely and/or automatically determining NAPL layer thickness discussed above, accuracy can be maintained despite significant changes in water table height. All equipment can be installed down well without concern for protection of above grade equipment. In addition, the equipment used in the systems and methods disclosed herein is, as compared with the prior art, easier to deploy and more robust, thus lessening the potential for damage due to, e.g., rough handling.

Figure 1A:
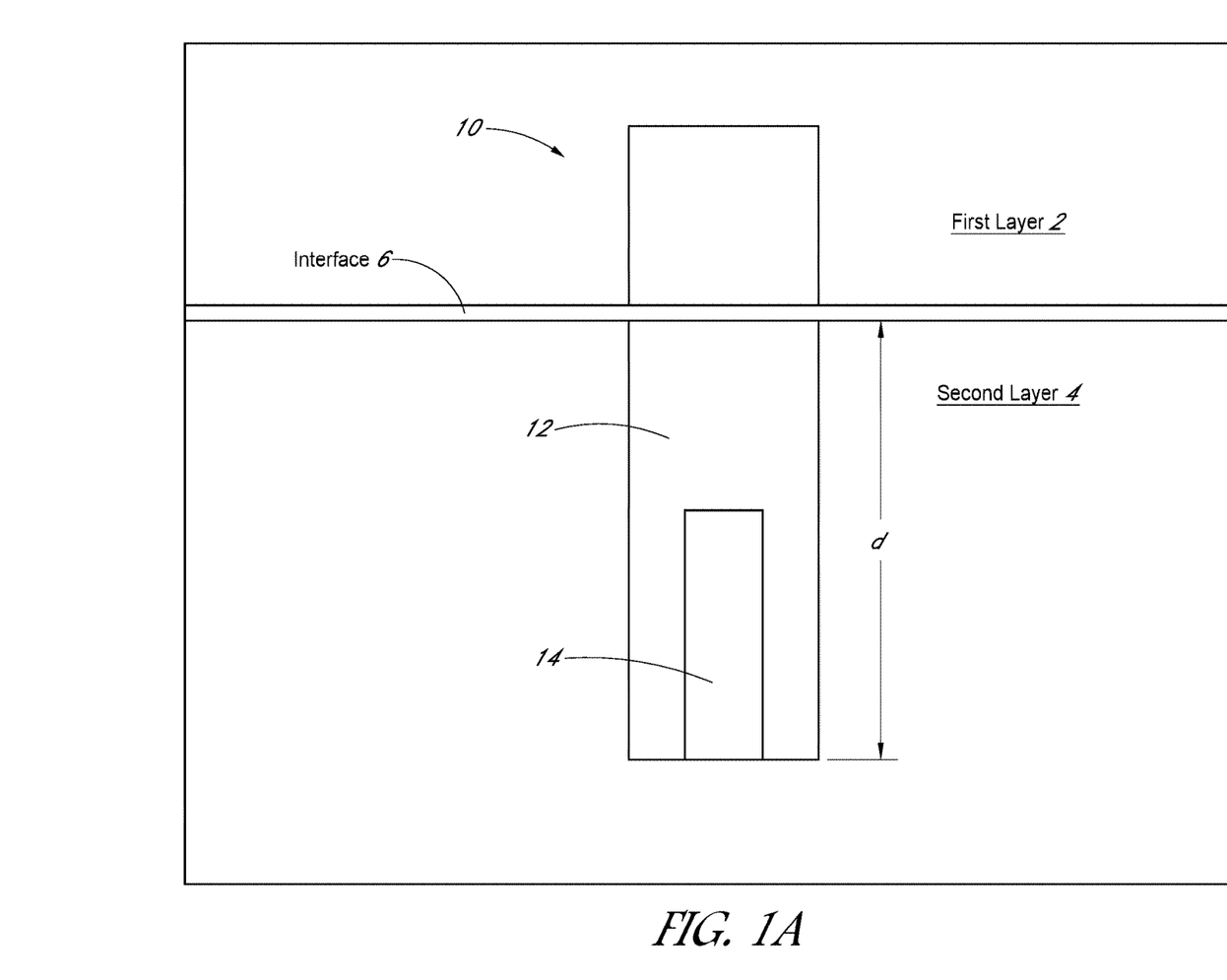
FIG. 1A is a schematic side view of a pressure transducer assembly, according to one embodiment.

FIG. 1A is a schematic side view of a pressure transducer assembly 10, according to one embodiment. In FIG. 1A, a first layer 2 of a NAPL is disposed adjacent (e.g., above) a second layer 4 of an aqueous phase liquid (APL), such as groundwater. In the illustrated embodiment, the first layer comprises a LNAPL, in which the NAPL is less dense than, and floats on top of, the APL. In other embodiments, however, such as that shown in FIG. 3, the second layer 4 of APL can be disposed above the first layer 2 of the NAPL for situations in which the NAPL comprises a DNAPL. The first and second layers 2, 4 contact or meet one another along an interface 6 (e.g., a NAPL/APL interface). The first layer 2 can have a thickness extending above the second layer to an air interface above both layers. As explained above, it can be important to monitor the thickness of the first layer 2 of NAPL.

The pressure transducer assembly 10 can comprise a floatable member 12 and a first pressure transducer 14 (referred to herein as a "variable transducer") can be coupled with the floatable member 12. In the illustrated embodiment, the first pressure transducer 14 can be integrated with the floatable member 12, such that, for example, the floatable member 12 can serve as a housing or support structure for the first pressure transducer 14. The floatable member 12 can provide fluid communication to the first pressure transducer 14 so that the first pressure transducer 14 can interact with the fluid to measure the relevant pressure(s). The first pressure transducer 14 can include suitable components for measuring the pressure of the liquid column above a port (not shown) of the transducer 14. The port can provide fluid communication to the fluid to enable the pressure transducer 14 to measure the pressure. For example, the transducer 14 can include a pressure sensor (not shown in FIG. 1A) and a data interface for communicating pressure data to a user. Any suitable type of pressure sensor can be used. In some embodiments, the data interface can comprise an electronic or optical interface that can be physically connected to a user's computing device. For example, in some embodiments, the computing device that receives the pressure data from the pressure sensor can calculate the thickness, or a change in thickness, of the first layer 2 of the NAPL based on the pressure measurements. In other embodiments, the data interface can comprise a wired or wireless communications device for transferring measured data to the user's computing device. In various embodiments, additional electronics can be provided for preprocessing raw sensor data.

The aggregate or total density of the pressure transducer assembly 10, which accounts for the respective densities of the floatable member 12 and first pressure transducer 14, can be selected to have a value between a first density value of the NAPL of the first layer 2 and a second density value of the APL of the second layer 4. For example, the floatable member 12 can be shaped to have the desired total density, and/or ballast can be added to or removed from the floatable member 12 to provide the desired total density. Still other ways of providing the desired total density may be suitable. In such an arrangement, the pressure transducer assembly 10 can be configured to float with or maintain a steady position relative to the interface 6 as the depth of the interface 6 changes (for example, due to variations in the thickness of NAPL in a well).

Thus, as shown in FIG. 1A, the transducer assembly 10 can serve as a variable-depth transducer, or variable transducer, so as to rise and fall with the interface 6. As shown, the density and dimensions of the transducer assembly 10 are selected such that the transducer assembly 10 spans the interface 6 (e.g., a first portion of the transducer assembly 10 extends into the first layer 2, and a second portion of the transducer assembly 10 extends into the second layer 4). As shown in FIG. 1A, a distance d of a submerged end of the transducer assembly 10 can remain constant relative to the interface 6 regardless of how the interface 6 moves up or down. As explained herein, due to the relatively constant value of the distance d, the transducer 14 can accordingly measure the head pressure associated with the first layer 2. It should be appreciated that the distance d may be considered constant even in situations in which the distance d changes slightly. For example, the distance d is relative to the desired accuracy of the measurement and may be considered constant when it varies by an amount less than 100% of an overall length of the transducer assembly 10, by an amount less than 50% of the overall length of the transducer assembly 10, or by an amount less than 10% of the overall length of the transducer assembly 10. In various embodiments, the distance d can vary in a range of 5 cm to 15 cm, or in a range of 7.5 cm to 12.5 cm (e.g., by about 10 cm) if a 20-cm accuracy is desired. Accordingly, d may not be a function of relative or absolute thickness of the first and second layers 2, 4, but rather may float with the interface 6.

In embodiments in which the first layer 2 comprises a LNAPL, the total density of the pressure transducer assembly 10 can be in a range of 50% to 99.5% of the second density value associated with the APL (such as water). For example, the total density of the pressure transducer assembly 10 can be in a range of 60% to 99.9%, in a range of 60% to 99.5%, in a range of 60% to 95%, in a range of 65% to 99.5%, in a range of 65% to 95%, in a range of 75% to 99.5%, in a range of 75% to 95%, in a range of 85% to 99.5%, in a range of 90% to 99.5%, in a range of 85% to 97.5%, in a range of 85% to 95%, or in a range of 90% to 95% of the second density value. By contrast, for embodiments in which the first layer 2 comprises a DNAPL, the total density of the pressure transducer assembly 10 can be in a range of 50% to 99.5% of the first density value associated with the DNAPL. For example, the total density of the pressure transducer assembly 10 can be in a range of 60% to 99.9%, in a range of 60% to 99.5%, in a range of 60% to 95%, in a range of 65% to 99.5%, in a range of 65% to 95%, in a range of 75% to 99.5%, in a range of 85% to 99.5%, in a range of 90% to 99.5%, in a range of 85% to 97.5%, in a range of 85% to 95%, or in a range of 90% to 95% of the first density value.

In embodiments in which the first layer 2 is a LNAPL, for example, the total density of the pressure transducer assembly 10 can be in a range of 0.6 g/cc to 0.999 g/cc, in a range of 0.6 g/cc to 0.995 g/cc, in a range of 0.6 g/cc to 0.95 g/cc, in a range of 0.65 g/cc to 0.995 g/cc, in a range of 0.65 g/cc to 0.95 g/cc, in a range of 0.75 g/cc to 0.995 g/cc, in a range of 0.75 g/cc to 0.95 g/cc, in a range of 0.85 g/cc to 0.995 g/cc, in a range of 0.9 g/cc to 0.995 g/cc, in a range of 0.85 g/cc to 0.975 g/cc, in a range of 0.85 g/cc to 0.95 g/cc, or in a range of 0.9 g/cc to 095 g/cc. In some embodiments, for example in which the APL is saltwater, the overall density of the pressure transducer assembly 10 can be in a range of 0.9 g/cc to 1.03 g/cc, in a range of 0.95 g/cc to 1.03 g/cc, in a range of 1 g/cc to 1.03 g/cc, in a range of 1 g/cc to 1.025 g/cc, in a range of 1 g/cc to 1.015 g/cc, or in a range of 1 g/cc to 1.01 g/cc. In various embodiments, the overall specific gravity of the pressure transducer assembly 10 as compared to water (e.g., as compared to freshwater, as compared with saltwater, or as compared with brackish water) can be in a range of 0.6 to 0.999, in a range of 0.6 to 0.995, in a range of 0.6 to 0.95, in a range of 0.65 to 0.995, in a range of 0.65 to 0.95, in a range of 0.75 to 0.995, in a range of 0.75 to 0.95, in a range of 0.85 to 0.995, in a range of 0.9 to 0.995, in a range of 0.85 to 0.975, in a range of 0.85 to 0.95, or in a range of 0.9 to 095.

In embodiments in which the first layer 2 is a DNAPL, the total density of the pressure transducer assembly 10 can be in a range of 1.001 g/cc to 6 g/cc, in a range of 1.001 g/cc to 5.5 g/cc, in a range of 1.001 g/cc to 3 g/cc, in a range of 1.001 g/cc to 2 g/cc, in a range of 1.005 g/cc to 1.8 g/cc, in a range of 1.005 g/cc to 1.5 g/cc, in a range of 1.005 g/cc to 1.2 g/cc, in a range of 1.001 g/cc to 1.1 g/cc, in a range of 1.005 g/cc to 1.1 g/cc, in a range of 1.001 g/cc to 1.05 g/cc, in a range of 1.005 g/cc to 1.05 g/cc, in a range of 1.001 g/cc to 1.04 g/cc, in a range of 1.005 g/cc to 1.04 g/cc, in a range of 1.01 g/cc to 1.04 g/cc, or in a range of 1.005 g/cc to 1.03 g/cc.

Figure 1B:
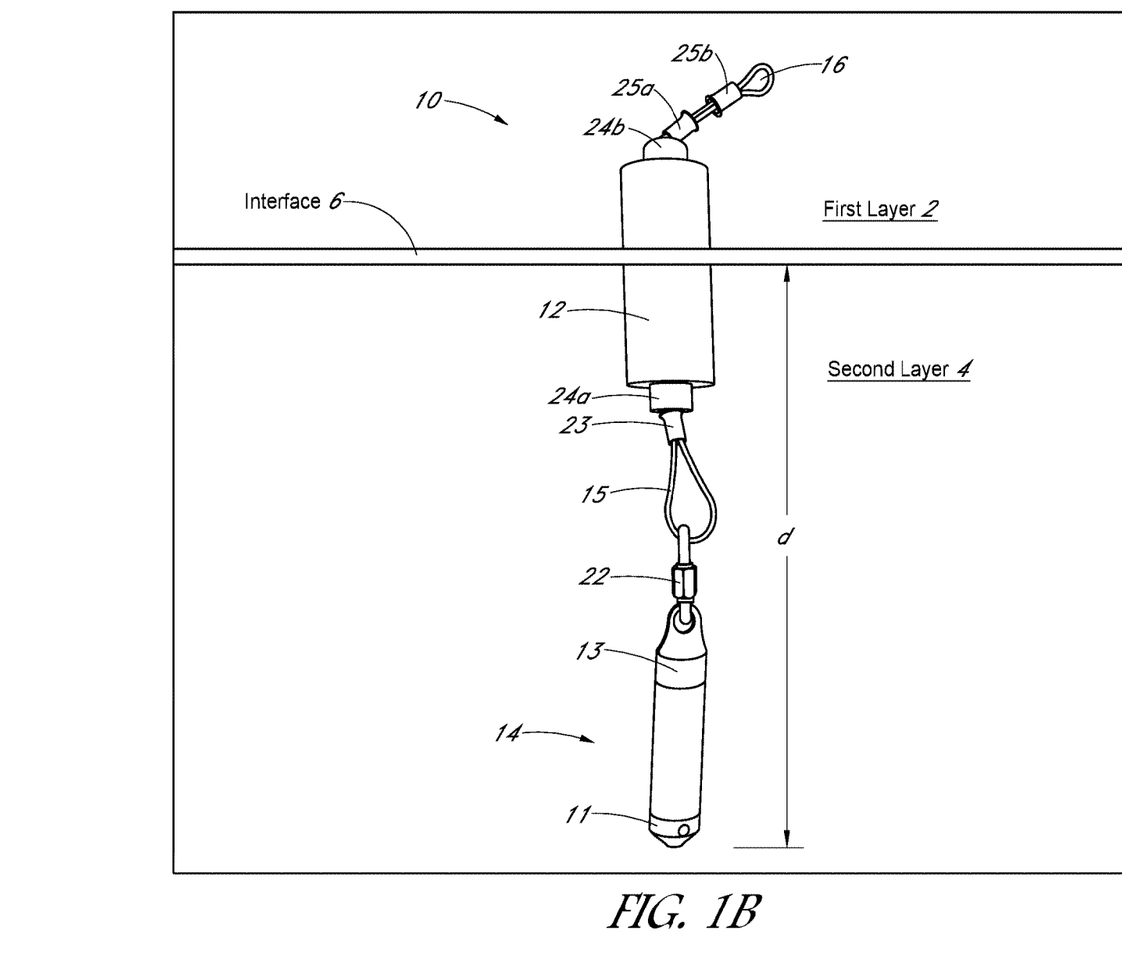
FIG. 1B illustrates a rendered image showing a pressure transducer assembly, according to another embodiment.

FIG. 1B illustrates a rendered image showing a pressure transducer assembly 10, according to another embodiment. In the embodiment of FIG. 1B, the pressure transducer assembly 10 can include the first pressure transducer 14 (e.g., the variable transducer) connected to the float or floatable member 12 by way of an elongate connector 15. A retrieval loop 16 can be provided at the upper end of the floatable member 12 to assist in retrieving or removing the assembly 10 from a well or other liquid-containing structure after use.

In FIG. 1B, therefore, the first pressure transducer 14 can be suspended below the floatable member 12 such that the first pressure transducer 14 is disposed at a greater depth than the floatable member 12. The first pressure transducer 14 can include a pressure sensor 11 disposed at the bottom end of the first pressure transducer 14. The pressure sensor 11 can comprise any suitable type of sensing device configured to transduce or measure a head pressure of liquid above the sensor 11. Although the sensor 11 is shown at the bottom end of the transducer 14, in other arrangements, the sensor 11 can be positioned at other locations along or within the transducer 14. The first pressure transducer 14 can further include internal data storage and a data interface 13 for communicating recorded pressure data to a user. As explained above, in some embodiments, the data interface 13 can comprise an electronic or optical interface that can be physically connected to a user's computing device (for example, a Universal Serial Bus, or USB, connector). In other embodiments, the data interface 13 can comprise a wired or wireless communications device for transferring measured data to the user's computing device. In various embodiments, additional electronics can be provided for preprocessing raw sensor data from the pressure sensor 11.

As with the embodiment of FIG. 1A, the aggregate or total density of the combined transducer assembly 10 (e.g., including the transducer 14 and the floatable member 12) can be between the densities of the first and second layers 2, 4. In the embodiment of FIG. 1B, in which the NAPL comprises a LNAPL, the aggregate or total density is greater than that of the LNAPL of the first layer 2 but less than that of the second layer 4 (e.g., water). As explained herein, it should be appreciated that the assembly 10 may also be configured for use in situations in which the first layer 2 comprises a DNAPL. The variable transducer assembly 10 is thus allowed to float freely with the interface 6 when deployed. As explained above, the position or distance d of the variable transducer assembly 10 remains constant relative to the LNAPL/water interface 6 throughout its deployment, even when the fluid levels of water and/or LNAPL change. Consequently, the pressure data collected by the transducer assembly 10 (e.g., by the pressure sensor 11) is associated with the LNAPL head pressure and the head pressure of the portion of the APL layer that overlies the bottom of the pressure transducer assembly 10. The pressure transducer assembly 10 can accordingly be used to measure or estimate a thickness t of the first layer 2 of LNAPL.

Figure 2:
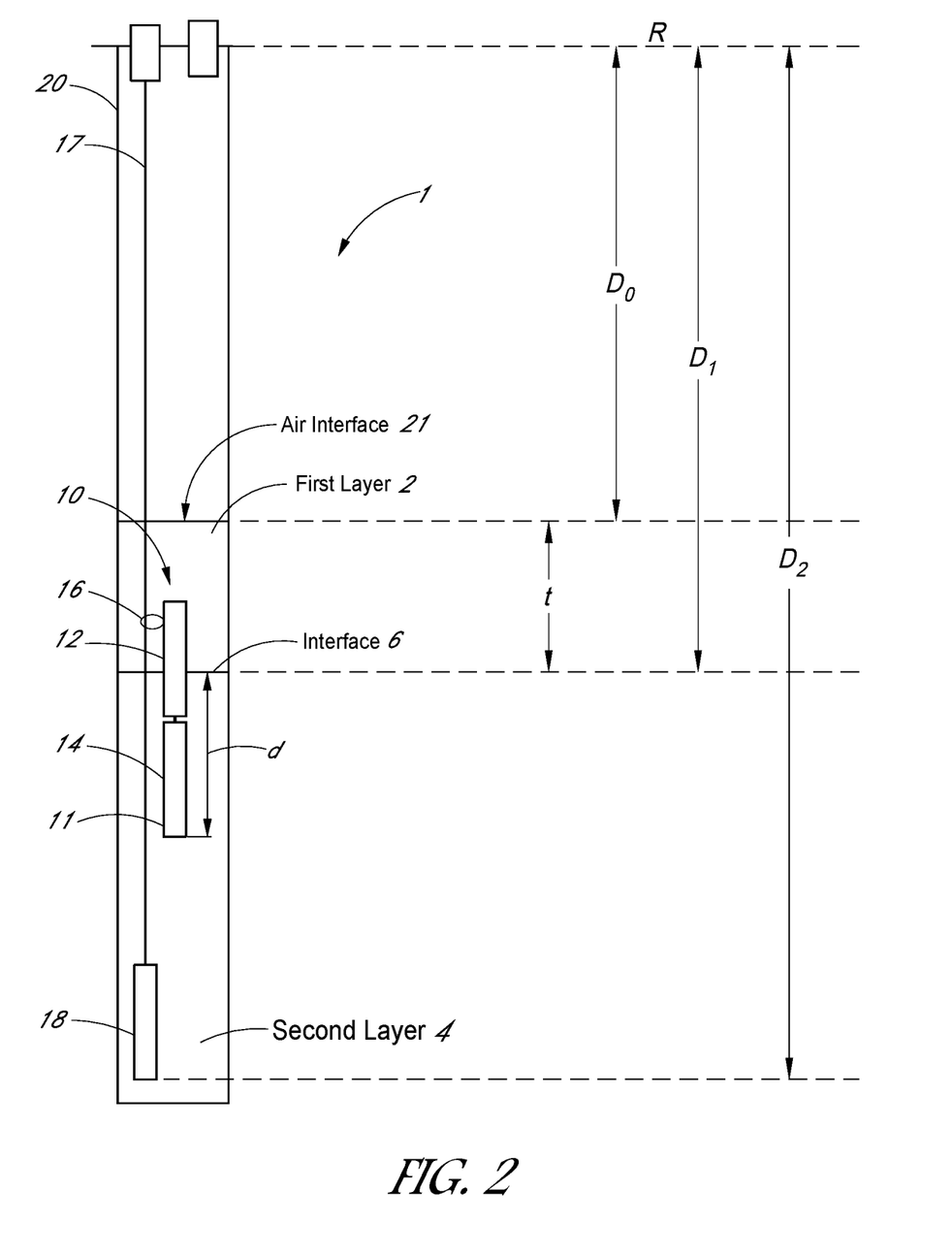
FIG. 2 is a schematic side view of a system for measuring a thickness of a LNAPL layer.

FIG. 2 is a schematic side view of a system 1 for measuring a thickness of a LNAPL layer, e.g., in situations in which the first layer 2 is less dense than, and floats on top of, the second layer 4. FIG. 2 also illustrates an air interface 21 between the first layer 2 of LNAPL and the air above. As shown, the air interface 21 can be at a depth $D_0$ relative to a reference position R, such as the ground level, which depth can vary over time. The system 1 can include the pressure transducer assembly 10 shown in FIG. 1B, although it should be appreciated that in other embodiments, the pressure transducer assembly 10 of FIG. 1A can be used. In the arrangement of FIG. 2, the system 1 is deployed in a well 20 (such as a groundwater monitoring well) that is drilled into the ground.

As with the embodiment of FIGS. 1A-1B, the pressure transducer assembly 10 can float along with the interface 6 to measure the head pressure of the LNAPL layer 2 above the interface 6. The interface 6 can be disposed at a first depth $D_1$ relative to the reference position R. Thus, the depth of the bottom end of the transducer assembly 10 (e.g., an approximate depth of the pressure sensor 11) may be $D_1+d$. As explained above, the first depth $D_1$ of the interface 6 may be variable, for example, due to rising or falling groundwater, etc.

To assist in estimating or measuring the depths $D_0$ and $D_1$, the system 1 can further include a second pressure transducer 18 (e.g., a fixed transducer) that is deployed below the LNAPL/water interface 6 at a second, fixed depth $D_2$ relative to the reference position R. The second pressure transducer 18 can measure the total head above the transducer 18, and based on the known depth $D_2$ of the second transducer 18, the measurements from the first transducer 14, and the density of the NAPL, the depths $D_0$, $D_1$ of the interfaces 21, 6 can be determined. As with the pressure transducer 14, the second pressure transducer 18 can include any suitable type of pressure transducer, data interface components, and/or processing circuitry to enable the transducer 14 to measure and transfer pressure data to a user's computing device. Data logging capabilities for both the variable and fixed transducers can be activated. The fixed transducer 18 records the total (overall) hydrostatic head in the well 20 above the transducer 18. The known density of the LNAPL in the well 20 can be employed to calculate the depth $D_0$ of the air/LNAPL interface 21 and the depth $D_1$ of the LNAPL/ groundwater interface 6 from the pressure data recorded by the transducers 14, 18.

Accordingly, the embodiments disclosed herein can beneficially enable the measurement or determination of the thickness t of the first layer 1, as well as the respective depths $D_0$, $D_1$ of the air-LNAPL and LNAPL-water interfaces 21, 6. For example, the thickness t of the first layer 1 of LNAPL can be determined as follows:

$$t=(P_1/SG_{APL}-d)(\rho_{NAPL}/\rho_{APL}),$$

wherein $P_1$ is a pressure measured by the first transducer 14 (which can be representative of the pressure exerted by the layer 1), $SG_{APL}$ is the specific gravity of the APL as compared with water, $\rho_{APL}$ is the density of the APL, $\rho_{NAPL}$ is the density of the NAPL, and the distance d. It should be appreciated that the units of pressure for $P_1$ in the above equation may be expressed in terms of units of length of water (e.g., cm $H_2O$, etc.).

The depths $D_0$, $D_1$ can also be determined by:

$$D_0=D_2-P_2-t(1-\rho_{NAPL}/\rho_{APL}); \text{ and}$$

$$D_1=D_0+t,$$

where $P_2$ is the pressure measured by the fixed transducer 18 (again, in units of lengths of water).

The embodiments are superior to the current typical practice of manual fluid level measurements because the air/LNAPL and LNAPL/groundwater interface data collected under both static and dynamic conditions using the disclosed embodiments have a higher resolution and accuracy compared to manual gauging. Beneficially, in various embodiments, the depth resolution of the system 1 can be in a range of 0.5 mm to 30 mm, in a range of 0.5 mm to 10 mm, in a range of 0.5 mm to 5 mm, in a range of 1 mm to 10 mm, in a range of 1 mm to 5 mm, in a range of 1 mm to 3 mm, in a range of 1.5 mm to 30 mm, in a range of 1.5 mm to 15 mm, in a range of 2.25 mm to 10 mm, in a range of 2.75 mm to 9 mm, or in a range of 3 mm to 6 mm. The disclosed systems and methods of remote and automated LNAPL thickness data collection therefore overcomes challenges associated with the data collection methods described above.

One example embodiment (such as that shown in FIGS. 1B and 2) can include at least the following components:
One (1) Van Essen Micro-Diver pressure transducer (variable transducer 14) instrument;
One (1) stainless steel threaded quick link (quick link);
One (1) closed cell Nitrophyl® cylindrical float with a 1.25-inch outer diameter (OD), a 3-inch length, and a 3/16-inch diameter round pass-through hole (floatable member 12);
Three (3) 316 stainless steel wire rope compression sleeves (compression sleeves);
Two (2) cylindrical rubber bumpers with a 5/8-inch OD, a 3/8-inch length, and a 1/8-inch diameter round pass-through hole (bumper);
One (1) approximately 1-foot length of 3/16-inch 316 stainless steel coated wire rope (wire rope); and
A second pressure transducer (fixed transducer 18) instrument.

The system 1 can be assembled and installed in the well 20 as shown in FIGS. 1B and 2. The variable transducer 14 can be connected to a link 22 (FIG. 1B) to facilitate removal and replacement of the assembly 10. One end of the elongate connector 15 (such as a wire rope) can be looped through the link 22 and secured using a compression sleeve 23 (lower loop). The other end of the elongate connector 15 (wire rope) can be threaded through a first bumper 24a (which rests on the compression sleeve 23), then through the floatable member 12, and through a second bumper 24b. The bumpers 24a, 24b protect the rounded sides of the floatable member 12 from abrasion by the cut ends of the elongate connector 15. The end of the elongate connector 15 can be secured in the retrieval loop 16 using two additional compression sleeves 25a, 25b. The first compression sleeve 25a secures the second bumper 24b against the floatable member 12; the second compression sleeve 25b reduces the diameter of the retrieval loop 16, for example, to approximately 1/4-inch in one example embodiment.

As shown in FIG. 2, during deployment of the system 1 in the well 20, a support cable 17 (such as a steel support cable) can be threaded through the retrieval loop 16 of the pressure transducer assembly 10. An object larger than the retrieval loop diameter can be connected to the bottom end of the support cable 17. The object "catches" the retrieval loop 16 during retrieval of the transducer assembly 10, so as to remove the transducer assembly 10 from the well 20. Any object of sufficient size and chemical compatibility (such as a stainless steel washer) may be used. However, the second transducer 18 (the fixed transducer) can be deployed to serve as the retrieval object and to collect the total head pressure data used to calculate the potentiometric surface.

In alternate embodiments, other materials could be utilized for the floatable member (such as stainless steel for a portion of the floatable member) to increase durability. Also, loops for transducer attachment and assembly retrieval can be welded onto the floatable member, so as to eliminate the need for separate components. Still other ways of assembling the pressure transducer assembly 10 may be suitable. Moreover, in other embodiments, the pressure transducer assembly 10 can be retrieved without the cable passing through the retrieval loop 16. For example, in some embodiments, a magnetic catch can be used and connected to a cable to retrieve the pressure transducer assembly 10 from the well 20.

Figure 3:
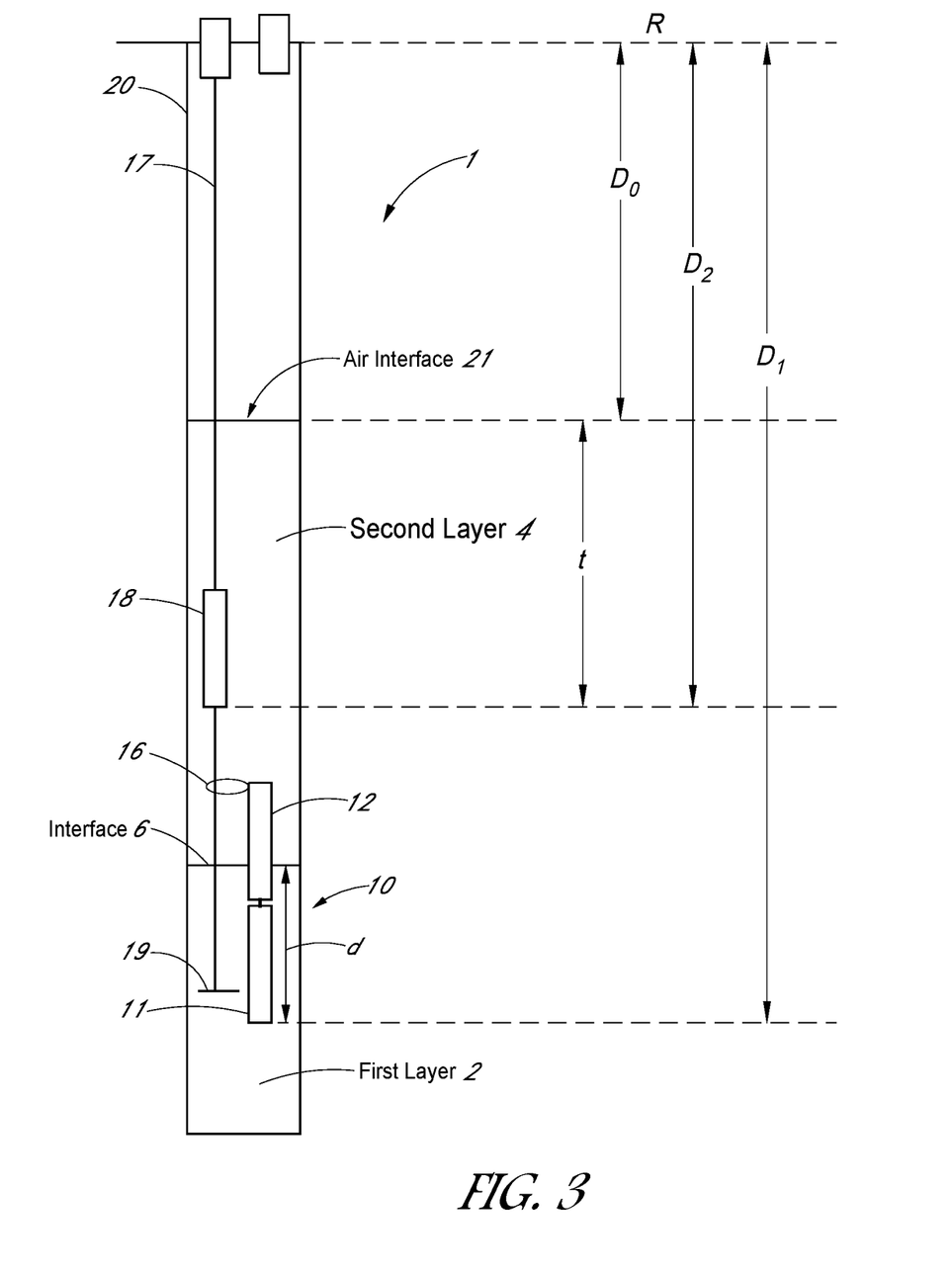
FIG. 3 is a schematic side view of a system for measuring a thickness of a DNAPL layer.

Moreover, in alternative embodiments, different transducer models can be used, provided the design of the float assembly is modified such that the density of the assembly is within an acceptable range. FIG. 3 is a schematic side view of a system 1 for measuring a thickness of a DNAPL layer, according to another embodiment. Unless otherwise noted, reference numerals in FIG. 3 represent components that are the same as or generally similar to like-numbered components of FIGS. 1A-2. Unlike the embodiment of FIG. 2, for example, in FIG. 3, the first layer 2 comprises a DNAPL and the second layer 4 comprises an APL that is less dense than the DNAPL, such that the second layer 4 is disposed over and floats on the first layer 2. As with the embodiment of FIG. 2, the overall density value of the pressure transducer assembly 10 can be between the density of the APL and DNAPL, but in the embodiment of FIG. 3, the overall density is greater than the density of the APL and less than the density of the DNAPL. As with the embodiment of FIG. 2, the pressure transducer assembly 10 of FIG. 3 can float at the interface 6 between the first and second layers 2, 4.

Altering the density of the floatable member 12 can enable the pressure sensor to float just below the water/DNAPL interface 6 to sense the pressure of the interface 6. As shown in FIG. 3, the second pressure transducer 18 (such as a fixed transducer) can be placed either above (as shown) or below the buoyant variable transducer assembly 10 to measure the thickness of the various layers. In addition, two buoyant sensors can be used so as to measure the thickness of both LNAPL and DNAPL layers if both are present in one well.

Additionally, in other embodiments, the entire assembly could be simplified. For example, in some embodiments, the transducer assembly 10 can be constructed such that its total density is greater than that of the LNAPL type(s) into which the assembly 10 would be deployed, but less than that of the APL (e.g., water), and such that there is, included in the assembly 10, an integrated retrieval system (e.g., a cable loop or other similar structure). This configuration may eliminate the use of a separate floatable member and may reduce the size of the assembly 10. As explained above, it should be appreciated that the density of the floatable member 12 can be adjusted by adding and/or removing ballast (for example, small weights such as BBs or bird shot to and/or from the floatable member 12. In some embodiments, the system 1 can include a kit or modular system including one or more floatable members 12 configured for use in, or having a density selected for, LNAPL environments, and one or more other floatable members 12 configured for use in, or having a density selected for, DNAPL environments. In other embodiments, the floatable member 12 can be shaped so as to adjust a total or overall density of the pressure transducer assembly 10.

In some embodiments, the system 1 can include a pressure transducer assembly 10 having an adjustable total density value. The adjustable total density value can be configured to be adjusted to a value between a first density value of the NAPL and a second density value of the APL. For example, in some embodiments, the pressure transducer assembly can include a receptacle for holding ballast and an access port for accessing the receptacle. A kit having one or more ballast elements to be added or removed from the receptacle can also be provided. The user can adjust the total density value of the pressure transducer assembly 10 by calculating the desired total or overall density for the pressure transducer assembly 10 based on the type of NAPL and APL at the site to be monitored, and, based on that calculation, determine an amount (and/or type) of ballast to add or remove from the receptacle to achieve the desired total density.

Figure 4:
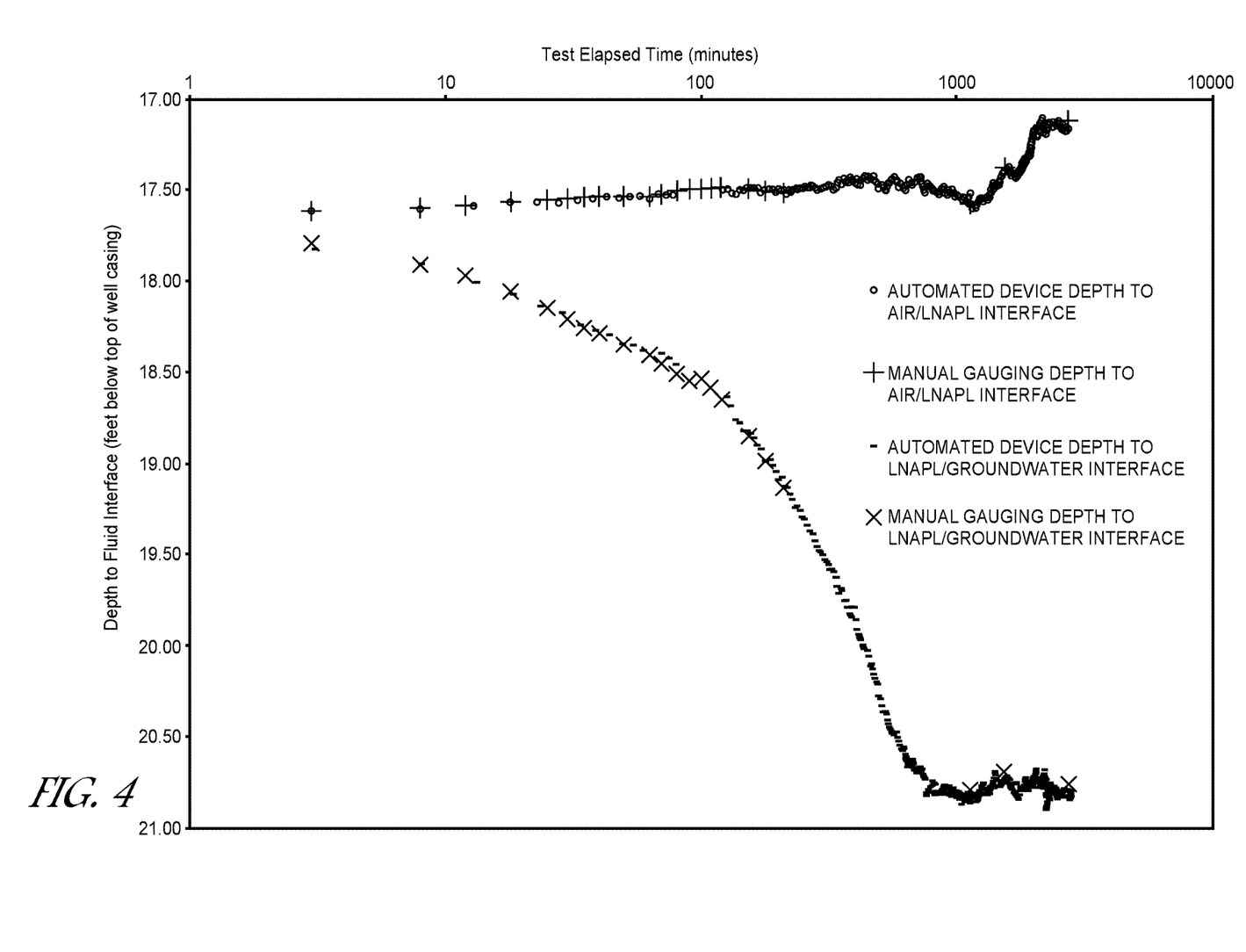
FIG. 4 is a chart showing fluid level data from a field trial of an embodiment of the system disclosed herein.

FIG. 4 is a chart showing fluid level data from a field trial of an embodiment of the system 1 disclosed herein. FIG. 4 shows actual measurements taken from a field test of the system 1. Note that there is extremely close agreement between the automated and manual determination of the depth $D_1$ to the LNAPL/water interface 6 as well as extremely close agreement between the automated and manual determination of the air/LNAPL interface 21.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A method for measuring a thickness of a first layer of nonaqueous phase liquid (NAPL) that is disposed adjacent a second layer of aqueous phase liquid (APL), such that an interface between the first and second layers is located at a first depth relative to a reference position, the method comprising:
   determining a first pressure exerted by the first layer with a first pressure transducer assembly including a first pressure transducer, the first pressure transducer assembly having a total density value between a first density value of the NAPL and a second density value of the APL; and
   calculating the thickness of the first layer based at least in part on the determined first pressure, a density of the NAPL, a density of the APL, and a distance between the interface and a pressure sensor used to measure the first pressure.

2. The method of claim 1, further comprising determining a second pressure associated with a second depth relative to the reference position with a second pressure transducer.

3. The method of claim 2, further comprising calculating the first depth based at least in part on the determined first pressure and the determined second pressure.

4. A method for measuring a thickness of a first layer of nonaqueous phase liquid (NAPL) that is disposed adjacent a second layer of aqueous phase liquid (APL), such that an interface between the first and second layers is located at a first depth relative to a reference position, the method comprising:
   determining a first pressure exerted by the first layer with a first pressure transducer assembly including a first pressure transducer, the first pressure transducer assembly having a total density value between a first density value of the NAPL and a second density value of the APL;
   determining a second pressure associated with a second depth relative to the reference position with a second pressure transducer; and
   calculating the thickness of the first layer based at least in part on the determined first pressure.

5. The method of claim 4, further comprising calculating the first depth based at least in part on the determined first pressure and the determined second pressure.

6. A method for measuring a thickness of a first layer of nonaqueous phase liquid (NAPL) that is disposed adjacent a second layer of aqueous phase liquid (APL), such that an interface between the first and second layers is located at a first depth relative to a reference position, the method comprising:
   determining a first pressure exerted by the first layer with a first pressure transducer assembly including a first pressure transducer, wherein the first pressure transducer assembly floats with the interface; and
   calculating the thickness of the first layer based at least in part on the determined first pressure, a density of the NAPL, a density of the APL, and a distance between the interface and a pressure sensor used to measure the first pressure.

7. The method of claim 6, further comprising determining a second pressure associated with a second depth relative to the reference position with a second pressure transducer.

8. The method of claim 7, further comprising calculating the first depth based at least in part on the determined first pressure and the determined second pressure.

9. A method for measuring a thickness of a first layer of nonaqueous phase liquid (NAPL) that is disposed adjacent a second layer of aqueous phase liquid (APL), such that an interface between the first and second layers is located at a first depth relative to a reference position, the method comprising:
 determining a first pressure exerted by the first layer with a first pressure transducer assembly including a first pressure transducer, wherein the first pressure transducer assembly floats with the interface;
 determining a second pressure associated with a second depth relative to the reference position with a second pressure transducer; and
 calculating the thickness of the first layer based at least in part on the determined first pressure.

10. The method of claim 9, further comprising calculating the first depth based at least in part on the determined first pressure and the determined second pressure.

11. The method of claim 9, wherein the NAPL comprises a light nonaqueous phase liquid (LNAPL), the method comprising positioning the second pressure transducer at a fixed depth from the reference position and below the first pressure transducer assembly.

12. A system for measuring a thickness of a first layer of nonaqueous phase liquid (NAPL) that is disposed adjacent a second layer of aqueous phase liquid (APL) such that an interface between the first and second layers is located at a first depth relative to a reference position, the system comprising:
 a pressure transducer assembly having a total density value between a first density value of a target NAPL and a second density value of a target APL,
 wherein the pressure transducer assembly is configured to measure a first pressure associated with the pressure exerted by the first layer; and
 a second pressure transducer configured to measure a second pressure associated with a second depth relative to the reference position.

13. The system of claim 12, wherein the pressure transducer assembly is configured to float with the interface as the first depth of the interface changes.

14. The system of claim 12, wherein a distance of the pressure transducer assembly relative to the interface remains constant after movement of the interface.

15. The system of claim 12, wherein the total density value is in a range of 1.001 g/cc to 1.04 g/cc.

16. The system of claim 12, the system having a depth resolution in a range of 0.5 mm to 30 mm.

17. The system of claim 12, wherein the second depth is constant.

18. The system of claim 12, wherein the second depth is greater than the first depth.

19. The system of claim 12, wherein the NAPL comprises a dense nonaqueous phase liquid (DNAPL), and wherein the total density value is less than the first density value but greater than the second density value.

20. The system of claim 12, wherein the second pressure transducer is connected to the reference position by a cable, the cable extending through a retrieval loop connected to the pressure transducer assembly, such that when the cable is withdrawn through the retrieval loop, the second pressure transducer engages with the retrieval loop to retrieve the pressure transducer assembly.

21. The system of claim 12, wherein the total density value is in a range of 0.60 g/cc to 0.999 g/cc.

22. The system of claim 12, wherein the pressure transducer assembly further comprises a floatable member, the first pressure transducer coupled with the floatable member.

23. The system of claim 22, wherein the first pressure transducer is integrated with the floatable member.

24. The system of claim 22, wherein the first pressure transducer is coupled to the floatable member by way of an elongate connector, such that the first pressure transducer is disposed at a greater depth than the floatable member.

25. The system of claim 12, wherein the NAPL comprises a light nonaqueous phase liquid (LNAPL), and wherein the total density value is greater than the first density value but less than the second density value.

26. The system of claim 25, wherein the second pressure is associated with a total pressure exerted by the first layer and the second layer.

27. The system of claim 26, wherein the thickness of the first layer is calculated based at least in part on the first pressure, a density of the NAPL, a density of the APL, and a distance between the interface and a pressure sensor used to measure the first pressure.

\* \* \* \* \*